United States Patent [19]

Masuda et al.

[11] 4,254,213
[45] Mar. 3, 1981

[54] PROCESS FOR FORMING BLACK DYE IMAGES

[75] Inventors: Kosaku Masuda; Hajime Wada; Kiyoshi Yamashita, all of Hino, Japan

[73] Assignee: Konishiroku Photo Industry Co., Ltd., Tokyo, Japan

[21] Appl. No.: 115,809

[22] Filed: Jan. 28, 1980

[30] Foreign Application Priority Data

Feb. 6, 1979 [JP] Japan .................. 54/12555

[51] Int. Cl.$^3$ .................. G03C 7/00; G03C 1/40
[52] U.S. Cl. .................. 430/381; 430/548; 430/555; 430/565
[58] Field of Search .............. 430/565, 548, 381, 387, 430/555

[56] References Cited

U.S. PATENT DOCUMENTS

| | | | |
|---|---|---|---|
| 2,294,909 | 9/1942 | Jennings | 430/548 |
| 2,706,683 | 4/1955 | Sawdey | 430/548 |
| 3,615,509 | 10/1971 | Klein et al. | 430/457 |
| 3,674,490 | 7/1972 | Matejec | 430/376 |
| 3,834,908 | 9/1974 | Hara et al. | 430/548 |
| 4,189,321 | 2/1980 | Kojima et al. | 430/381 |

*Primary Examiner*—J. Travis Brown
*Attorney, Agent, or Firm*—Bierman & Bierman

[57] ABSTRACT

A process for forming a dye image is disclosed which comprises processing an image-wise exposed silver halide photographic emulsion with an aromatic primary amine color developing agent in the presence of bis pyrazolines obtained by reacting 3-acylamino-5-pyrazolones with para-hydroxybenzaldehydes having at least one of the ortho positions to the hydroxy group substituted with a member selected from halogen, alkyl, aryl, amino or amido groups. The invention includes the present dye forming coupler alone and combined with the silver halide emulsion layer.

18 Claims, No Drawings

PROCESS FOR FORMING BLACK DYE IMAGES

This invention relates to novel light-sensitive silver halide photographic materials and more particularly is concerned with light-sensitive silver halide photographic materials comprising photographic couplers capable of giving dye images of an excellent neutral black color.

Various methods have heretofore been proposed to obtain a neutral black dye image. For instance, West German Pat. Nos. 492,518 and 537,923 individually disclose a method of forming black dye images, wherein color development is carried out by using a mixture of such couplers as yellow, magenta and cyan, said couplers being commonly used at present in the color photography. In this method, however, it is difficult to obtain a black dye image which is neutral over all density region for such reason that these three color couplers are different from one another in coupling rate with a color developing agent, for example, paraphenylenediamine type color developing agents or p-aminophenol type color developing agents. West German Pat. No. 1,158,836 discloses a method of forming black dye images using 4-aminopyrazolinobenzimidazole developing agent, wherein an oxidation product of this developing agent formed during development is condensed with an active methylene compound to form a black dye image. According to this method, however, it is also practically difficult to obtain a dye image of a substantially neutral black color with a sufficiently high density.

Further, British Pat. No. 1,210,417 and U.S. Pat. No. 3,615,509 individually disclose a method relying on the use of developer couplers. In this method, a developing agent having in a molecule both a moiety of p-aminophenol developing agent and a moiety of phenolic coupler is used in the development of an exposed silver halide emulsion to form a polymerized dye at the exposed area, and the dye is subjected to chelation by means of an alkali bath or copper chelate bath treatment to obtain a dye image of a substantially black color with a sufficiently high density. In this method, however, there remain, as yet, many problems such as stability of a processing bath because of the use of the so-called developer couplers, pollution problem caused by using copper chelate, and stability of the resulting dye image.

Still further, U.S. Pat. No. 3,674,490 discloses a method of forming quinone type black dye images, wherein a silver image once obtained by the currently employed black-and-white photographic processing is allowed to undergo oxidation coupling reaction at the silver image portion with an aromatic hydroxyamino compound, while utilizing hydrogen peroxide as a reaction catalyst, and thereby to form the quinone type black dye. In this method, however, not only more processing baths are necessary but also a sufficient density is difficult to obtain under ordinary processing conditions.

An object of the present invention is to provide light-sensitive silver halide photographic materials capable of obtaining black image with excellent photographic characteristics, from which such drawbacks as mentioned above have been eliminated. More particularly the object of the invention is to provide light-sensitive silver halide photographic materials comprising couplers capable of forming dye images of a substantially black color on coupling with an oxidation product of an aromatic primary amine type color developing agent which is used as a color developing agent.

The object of the present invention can be accomplished by processing a silver halide with an aromatic primary amine color developing agent in the presence of bis type pyrazolones which are obtained by reacting 3-acylamino-5-pyrazolones with parahydroxybenzaldehydes, at least one of the ortho-positions of the hydroxy group of which has been substituted by a halogen atom, an alkyl, aryl, amino or amido group.

Of the above-mentioned bis type pyrazolones (hereinafter called "the present compounds"), those as represented by the following general formula [I] are particularly advantageously usable in the present invention.

General formula [I]

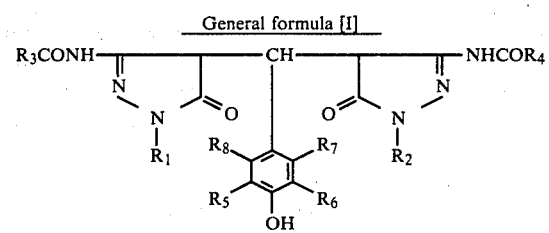

wherein $R_1$ and $R_2$ individually represent a hydrogen atom or unsubstituted chain or cyclic alkyl group (e.g. methyl, ethyl, isopropyl, t-butyl, t-octyl, cyclohexyl, norbonyl, etc.); or a substituted chain or cyclic alkyl group (the substituent of which is, for example, such as selected from a group consisting of halogen atoms, nitro, cyano, aryl, alkoxy, aryloxycarboxy, alkoxycarbonyl, aryloxycarbonyl, sulfo, sulfamoyl, carbamoyl, acyl, aminoureido, 5 or 6-membered heterocyclic containing a sulfur, oxygen or nitrogen atom, arylsulfonyloxy, and hydroxy groups, for example $\beta$-cyanoethyl, $\beta$-chloroethyl, benzyl, nitrobenzyl, dichlorobenzyl, $\gamma$-(2,4-di-t-pentylphenoxy)propyl, $\beta$-phenoxyethyl or the like). Further, $R_1$ and $R_2$ individually represent an unsubstituted aryl group (e.g. phenyl, $\alpha$- or $\beta$-naphthyl, etc.) or an aryl group having at least one substituent (the substituent is, for example, such as selected from the group consisting of alkyl, alkoxy, aryloxy, halogen atoms, carboxy, alkoxycarbonyl, acylamino, carbamoyl, alkylcarbamoyl, dialkylcarbamoyl, arylcarbamoyl, alkyl, sulfonamido, arylsulfonamido, cyano and nitro groups. Particularly useful substituent is a phenyl group (e.g. 2,4,6-trichlorophenyl, 2,6-dichloro-4-methoxyphenyl or the like groups). Still further, $R_1$ and $R_2$ individually represent a heterocyclic group (a 5- or 6-membered heterocyclic ring or condensed heterocyclic ring containing nitrogen, oxygen or sulfur atom as a heteroatom, for example, pyridyl, quinolyl, furyl, benzothiazolyl, oxazolyl, imidazolyl, naphthoxazolyl) or a heterocyclic group having been substituted by one of the substituents as enumerated above with respect to the aryl group. Preferable examples of $R_1$ and $R_2$ are individually above-mentioned aryl groups.

$R_3$ and $R_4$ individually represent an alkyl, substituted alkyl, aryl, substituted aryl, heterocyclic or substituted heterocyclic group, each having the same meaning as defined in the case of the aforesaid $R_1$ and $R_2$. Further, $R_3$ and $R_4$ individually represent an oxy group substituted with an alkyl or aryl group (e.g. methoxy, ethoxy, phenoxy, tolyloxy, etc.) or an amino group (e.g. substituted or unsubstituted N-alkylamino, cycloalkylamino, N,N-dialkylamino, N-alkyl-N-arylamino, N-arylamino). In these, an aryl and substituted aryl group are preferable. $R_5$ represents an alkyl, substituted alkyl, aryl, substituted aryl, each having the same meaning as defined in the case of the aforesaid $R_1$ and $R_2$, or an amino group having the same meaning as defined in the case of the aforesaid $R_3$ and $R_4$. Further, $R_5$ represents a halogen atom (e.g. fluorine, chlorine, bromine or iodine) or an amido group (e.g. acetamido, benzamido). $R_6$, $R_7$ and $R_8$ individually represents halogen atom, alkyl, aryl, substituted oxy, amino or amido group as defined hereinbefore or a hydrogen atom, and preferably $R_6$ is a halogen atom, alkyl, aryl, substituted oxy, or amino group, and $R_7$ and $R_8$ are individually a hydrogen atom. $R_5$ and $R_6$ are preferably branched alkyl groups, especially t-butyl and t-pentyl groups individually. The present compounds can be readily obtained according to the procedure as described in Japanese Laid-Open-to-Public Publication No. 105820/1976 by reacting arylaldehyde compound with 5-pyrazolone, and the synthesis of bis type couplers by this procedure is well known to those skilled in the art.

Accordingly, the present compounds of the general formula [I] can be readily obtained by the reaction between aldehydes represented by the following general formula [II] and 2 molecules of 3-acylamino-5-pyrazolones represented by the following general formula [III] or [IV].

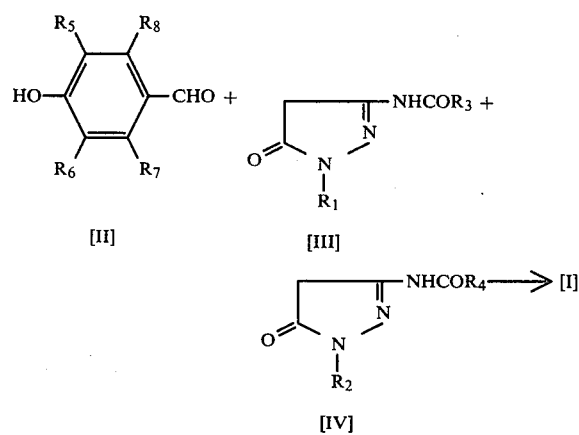

In the above formulas, $R_1$ through $R_8$ individually have the same meanings as defined in the general formula [I].

The aldehydes of the general formula [II] are of benzaldehyde having a hydroxy group, and should not be occupied by hydrogen atoms at the ortho-positions of the hydroxy group all together.

Typical examples of the aldehyde of the general formula [II] are exemplified below, but it should be construed that the starting compounds used for the synthesis of the present compounds are not limited thereto.

Exemplified compound

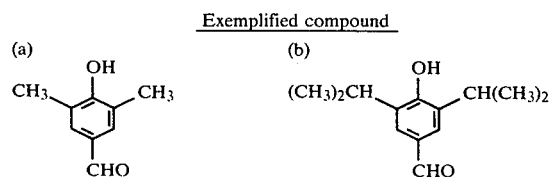

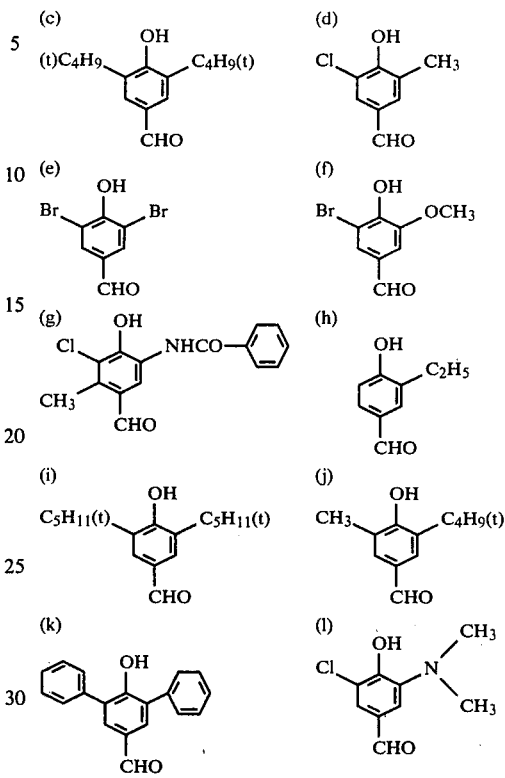

Exemplified below are typical examples of 3-acylamino-5-pyrazolone magenta coupler, but it should be construed that the starting compounds used for the synthesis of the present compounds are not limited thereto.

Exemplified compound

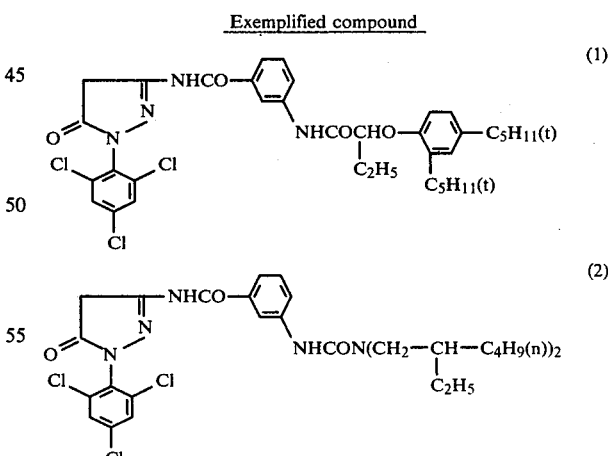

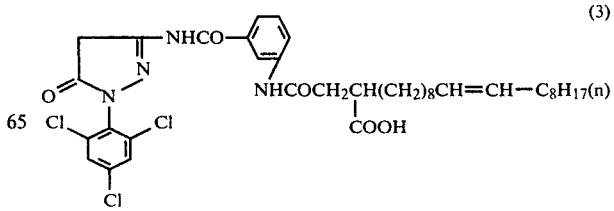

-continued
Exemplified compound
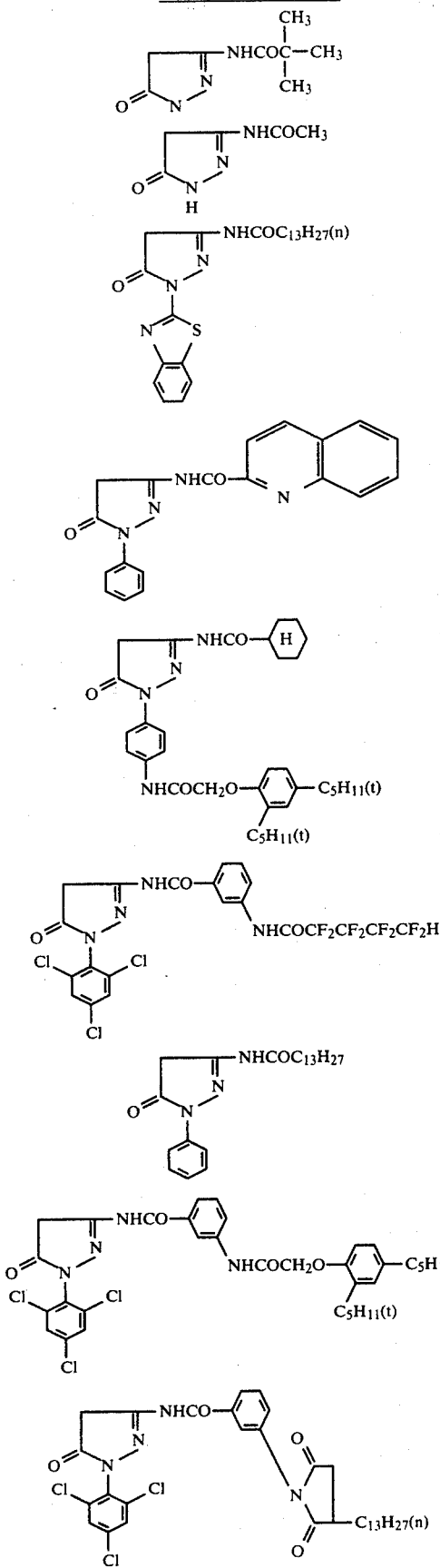
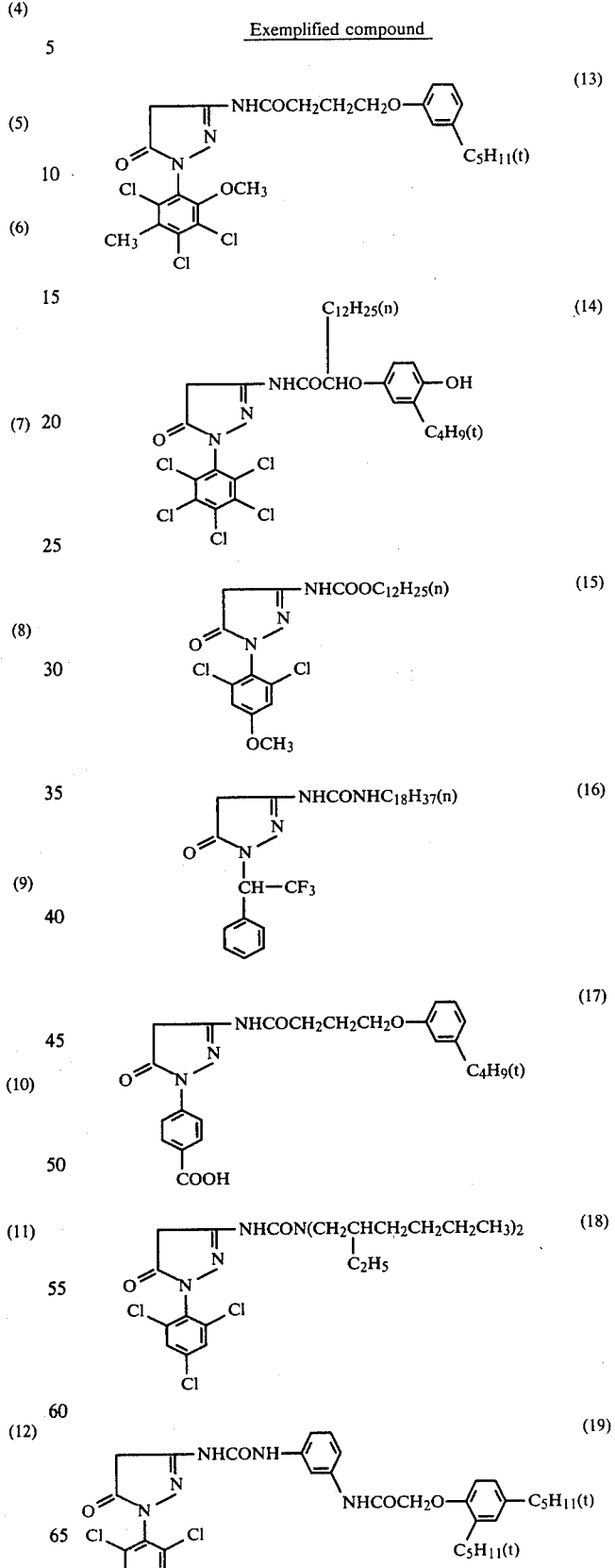

-continued
Exemplified compound
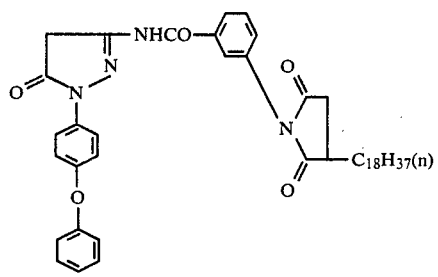
(20)
Typical examples of the present ocmpounds are exemplified below, but it should be construed that the compounds used in the present invention are not limited thereto.
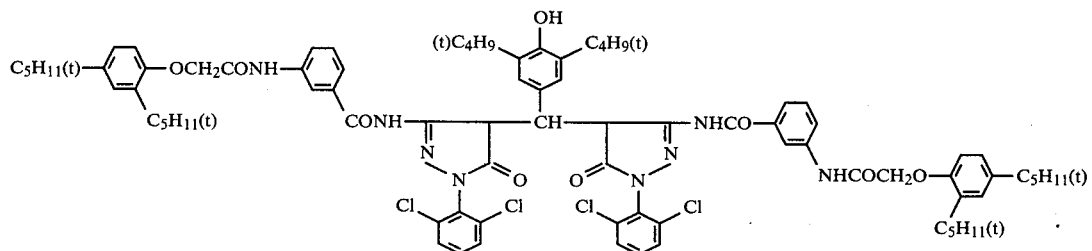
(21)
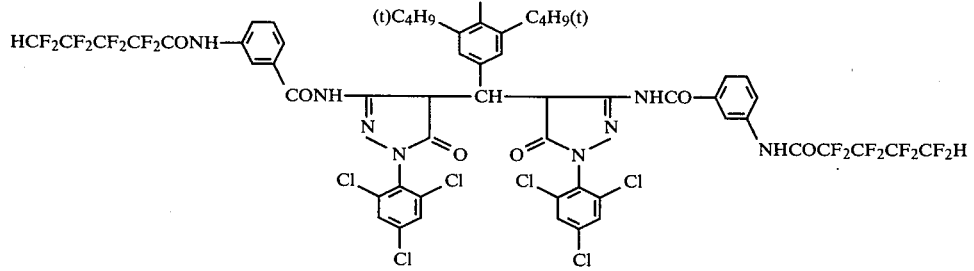
(22)
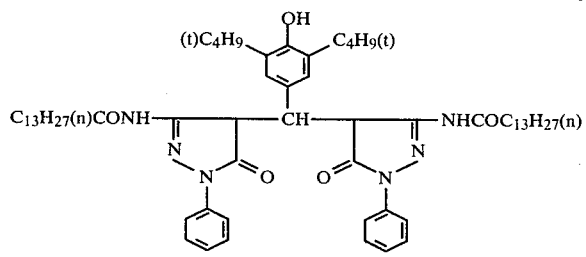
(23)
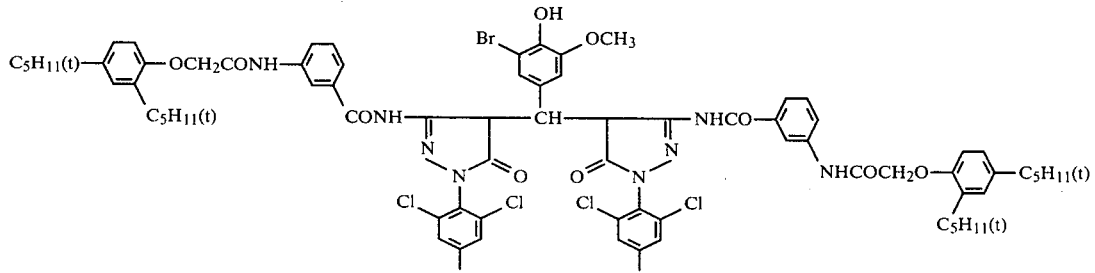
(24)

-continued

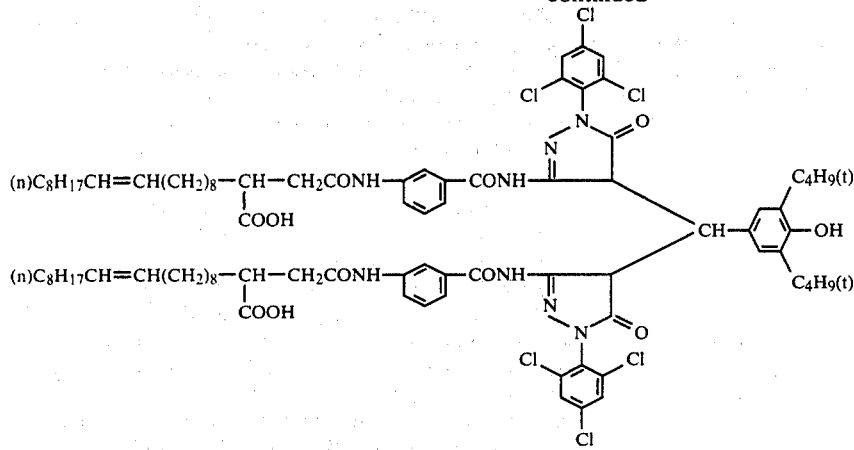

(25)

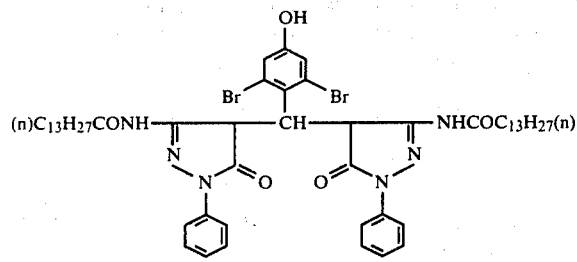

(26)

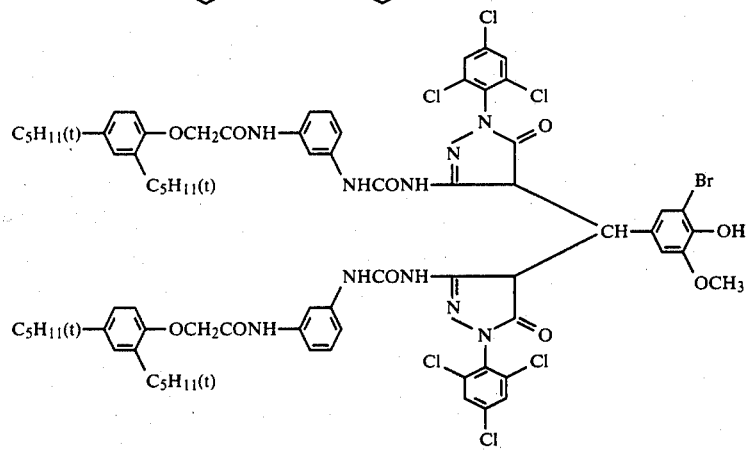

(27)

The reason why the present compounds form dye images of a substantially black color on coupling with an oxidation product of aromatic primary amine type color developing agents is not thoroughly clarified yet, but it is considered that at the time of coupling, a yellow dye, magenta dye and cyan dye are simultaneously formed. However, amounts of these three kinds of dyes thus formed are influenced by the composition of silver halide emulsion, the kind of developing agent, or pH or temperature of the developer used in the present invention. On that account, therefore, the amounts of these three kinds of dyes formed can be varied by changing the abovementioned influential factors, thereby readily obtaining a neutral black dye.

British Pat. Nos. 786,859 and 968,461 disclose bis type couplers which are obtained from the reaction between p-hydroxybenzaldehyde and 5-pyrazolone magenta coupler. Such bis type couplers however, do not give at all black dye images, because said couplers do not form yellow and cyan dyes even when they undergo coupling with an oxidation product of aromatic primary amine type color developing agents. That is, the aldehydes of the general formual [II] having a hydroxy group, the ortho-positions of said hydroxy group should not be occupied by hydrogen atoms all together, are used in the present invention, otherwise no object of the present invention can be accomplished.

The process for the synthesis of the present compounds is concretely illustrated below with reference to a synthesis example.

SYNTHESIS EXAMPLE 1

Preparation of exemplified compound (21)

To a solution of 1.3 g of 1-(2,4,6-trichlorophenyl)-3-3-(2,4-di-tert-pentylphenoxyacetamido)benzamido-2-pyrazoline-5-one and 240 mg of 4-hydroxy-2,6-di-tert-butylbenzaldehyde in 30 ml of ethanol is added 2 drops of triethylamine, and the resulting mixture is refluxed for 3 hours. After allowing the reaction mixture to cool, the deposit formed is collected by filtration and then dried to obtain 700 mg of colorless powder as the title compound.

Following the above-mentioned process, the present compounds other than exemplified compound (21) can be synthesized. Of the present compounds synthesized in the above manner, some of exemplified compounds are illustrated below with reference to melting points and elementary analysis values thereof as measured.

| Exemplified compound | Melting point (°C.) | | | C | H | N |
|---|---|---|---|---|---|---|
| (21) | 180–183 | Calculated | (%) | 61.67 | 6.44 | 7.62 |
| | | Found | (%) | 61.50 | 6.52 | 7.81 |
| (22) | 178–179 | Calculated | (%) | 46.67 | 3.23 | 7.65 |
| | (dec) | Found | (%) | 46.62 | 3.21 | 7.51 |
| (23) | 97–99 | Calculated | (%) | 74.20 | 9.19 | 8.51 |
| | | Found | (%) | 73.99 | 9.09 | 8.53 |
| (24) | 200–202 | Calculated | (%) | 58.69 | 4.99 | 7.21 |
| | | Found | (%) | 58.55 | 4.98 | 7.21 |

Forming a dye image by processing a silver halide emulsion in the presence of the present compound with an aromatic primary amine color developing agent can be achieved by allowing the present compound to be present at the time of color development in such a position that the present compound may participate in the color development reaction so as to form dyes as expected, and this formation of the dye image may be embodied according to the conventional procedure known as the so-called inner type color photographic process or outer type color photographic process.

The present compound can be incorporated into a silver halide emulsion according to the technique commonly used in the conventional inner type color photographic process. For instance, the present compound is dissolved in a high boiling organic solvent having a melting point above 175° C., such as tricresyl phosphate or dibutyl phthalate, or in a low boiling organic solvent, such as ethyl acetate or butyl propionate, or in a mixed solvent thereof. Thereafter, the resulting solution is mixed with an aqueous gelatin solution containing a surface active agent, and the resulting mixture is emulsified by means of a high speed rotary mixer or colloid mill to prepare a dispersion. The dispersion is then incorporated into the silver halide emulsion. Alternatively, the aforesaid emulsified dispersion is set, followed by forming the dispersion thus set into noodle. The resultant may be incorporated, after removing the low boiling organic solvent therefrom by means of water-washing or the like, into the silver halide emulsion. Further, the incorporation into the silver halide emulsion of the present compound may be carried out according to the so-called Fischer dispersion method when said compound is alkali soluble. A light-sensitive silver halide photographic material having contained therein the present compound (hereinafter called "the present photographic material") usually contains a coupler represented by the general formula [I] in an emulsion layer or a layer adjacent thereto. The present photographic material, however, may contain two or more kinds of the present compounds or may contain ordinary yellow, magenta and cyan couplers, or phenols as disclosed in Japanese Laid-Open-to-Public Publication No. 46029/1978 in combination with the present compound or compounds.

On development of the present photographic material with a common aromatic primary amine type color developing agent, the exposed silver halide grains are reduced with the color developing agent to form a silver image and, on the other hand, the oxidized color developing agent undergoes coupling with the present compound which is a coupler to form a mixture of dyes, said mixture will come to assume a black color. Accordingly, a light-sensitive silver halide photographic material having contained therein the present compound is to give a substantially black dye image through the processing system comprising color development fixing and water-washing, and bleaching if necessary. Usable as the developing agent in this processing system is any of the currently available aromatic primary amine type color developing agents. Particularly preferable color developing agents include such developing agents of p-aminophenol type or p-phenylenediamine type, for example, as N,N-diethyl-p-phenylenediamine, N-ethyl-N-ω-sulfobutyl-p-phenylenediamine, 2-amino-5-diethylaminotoluene, p-amino-N-ethyl-N-β-hydroxyethylaniline, 4-amino-3-methyl-N-ethyl-N-(β-hydroxyethyl)aniline, 4-amino-3-methyl-N-ethyl-N-(β-methoxyethyl)aniline, 4-amino-3-methyl-N-ethyl-N-(β-methylsulfonamidoethyl)aniline or p-aminophenols (e.g. p-aminophenol).

In the present invention, there may also be used such so-called DeV-DeV compounds, for example, as 2,2'-methylenebis (p-aminophenol), N,N'-ethylenebis(4-amino-3-methyl-N-ethylaniline), etc.

Advantageously usable as hydrophilic colloid for preparing a photosensitive emulsion to be used in the present photographic material are gelatin, gelatin derivatives and other known materials.

Usable as silver halide in the present photographic material are any of silver halides commonly used in ordinary silver halide photographic emulsions, such as silver bromide, silver chloride, silver iodobromide, silver chlorobromide, silver chloroiodobromide, etc.

The silver halide emulsion used in the present photographic material may be prepared by various procedures, for example, a procedure as disclosed in Japanese Patent Publication No. 7772/1971 or a procedure as disclosed in U.S. Pat. No. 2,592,250, that is, a process for preparing the so-called conversion emulsions or the so-called Lippmann's emulsions, including of course usually employed procedures for the preparation of silver halide photographic emulsions. This silver halide emulsion can be chemically sensitized by known means as well as stabilized by means of such compounds as triazoles, imidazoles, azaindenes, benzothiazolium compounds or mercaptans or mixtures thereof, and the emulsion may also contains sensitizing compounds of thioether type, quaternary ammonium salt type or polyalkylene oxide type. Further, this silver halide emulsion may contain wetting agents, plasticizers, agents for improving physical properties of coatings or the like, for example, such dihydroxyalkane as glycerine, 1,5-pentadiol, etc., esters of ethylenebisglycolic acid, bisethoxydiethyleneglycol succinate, and water-dispersible particulate high molecular compounds obtained by emulsion polymerization. The silver halide emulsion may further contain film hardeners such as etheleneimine type compounds, dioxane derivatives, dicarboxylic acid chlorides, diesters of methanesulfonic acid, etc., coating aids such as saponin, salts of sulfosuccinic acid, etc., fluorescent whitening agents, antistatic agents, antistain agents, etc.

The silver halide emulsions used in the present invention may be optically sensitized by means of appropriate sensitizing dyes in order to impart photosensitivity to the emulsion at their respective wavelength regions as desired. Usable as sensitizing dyes in the silver halide emulsions of the present invention are those various in kind, and these dyes may be used either singly or in combination of two or more.

The present photographic materials may further contain, if necessary, a variety of photographic additives other than such compounds as referred to hereinbefore. For instance, into the photosensitive emulsion layer or layer adjacent thereto may be incorporated, according to the object aimed at, a compound which releases a development inhibitor in response to density of an image at the time of development, for example, such development inhibitor releasing compounds as disclosed in Japanese Patent Publication No. 22514/1971, or tetrazolium compounds.

The present photographic materials are prepared by coating a silver halide photographic emulsion having contained therein a variety of photographic additives referred to previously on a support which has been subjected to corona discharge treatment, flame treatment or ultraviolet irradiation treatment, or on a support through a sub layer or intermediate layer.

Advantageously usable supports for the preparation of the present photographic materials include, for example, baryta paper, polyethylene-coated paper, glass plate, and films of cellulose acetate, cellulose nitrate, polyethylene terephthalate, etc., including films of polyamide, polycarbonate, polystyrene, etc., and the desired support may be selected from among these materials according to the purpose for which the resulting photographic material is used.

In carrying out the process of the present invention, preferably the present compound is incorporated into a silver halide photographic emulsion layer of the present photographic material, and then the photographic material after exposure is advantageously color developed according to the ordinary color development process applicable to the so-called inner type light-sensitive silver halide photographic material. To the process of the present invention, however, the so-called outer type color treatment process is also applicable.

A developer of the following composition as an illustration is typical of the inner type color developer.

| [Composition of developer] | |
|---|---|
| Sodium carbonate monohydrate | 10 g |
| Sodium sulfite | 2 g |
| Potassium bromide | 1 g |
| 4-Amino-N,N-diethylaniline sulfate | 6 g |
| Water to make | 1 liter |
| | pH 11.0 |

The inner type color developers may also contain one or more of black-and-white developing agents, for example, methol, phenidone, hydroquinone, etc., according to the use of the resulting photographic material.

The present photographic materials, after color development may be subjected to the usual photographic treatment which comprises using a suitable combination of a bleach, a stopper containing an organic acid, a stop-fixer containing fixing agent such as an organic acid and hypo or ammonium thiosulfate, a fixer containing a fixing agent such as hypo or ammonium thiosulfate, and other treatments with a stabilizer and the like, including water-washing and drying.

The present photographic materials are advantageously usable as photosensitive black-and-white photographic materials for the preparation of general black-and-white photographic negatives, general black-and-white photographic printing paper or photographic materials for X-ray photography, lithophotographic materials, general photographic materials for microphotography, etc.

The process of the present invention is also applicable to an image amplifying treatment method as disclosed, for example, in Japanese Patent Publication No. 46419/1974 and Japanese Laid-Open-to-Public Publications Nos. 7929/1976, 16023/1976 and 36136/1976, and a drastic curtailment of silver in its amount used in the present photographic materials by application to the present process of this method.

Furthermore, the process of the present invention is also applicable to color photographic materials as disclosed, for example, in Japanese Laid-Open-to-Public Publication Nos. 133423/1978 and 53-133432.

That is, the present compounds may be incorporated into a light-sensitive silver halide photographic materials comprising a combination of a blue-sensitive silver halide emulsion layer containing a yellow dye forming coupler, a green-sensitive silver halide emulsion layer containing a magenta dye forming coupler and a red-sensitive silver halide emulsion layer containing a cyan dye forming coupler, all of said couplers being used in the silver halide color photographic process relying on the usual subtractive color mixing photographic process. The present compound, as an illustration of embodiments, may be incorporated into at least one of silver halide emulsion layers containing a cyan coupler, magenta coupler or yellow coupler. Further, the present compound may be incorporated, an another embodiment, into at least one silver halide emulsion layer provided apart from a silver halide emulsion layer containing a cyan coupler, magenta coupler or yellow coupler.

The present invention is concretely illustrated below with reference to example.

EXAMPLE 1

Each of exemplified compound (21) and comparative compounds as will be illustrated later, each amounting to 20 g, was completely dissolved in a mixed solvent comprising 20 ml of dibutyl phthalate and 40 ml of ethyl acetate while maintaining said mixed solvent at 60° C. The solution thus prepared was mixed with 10 ml of a 6% aqueous solution of Alkanol B (a product of alkylnaphthalene sulfonate produced and sold by Du Pont Co.) and 200 ml of a 5% aqueous gelatin solution, followed by dispersing with emulsifying by means of a colloid mill. Each of the dispersed coupler thus obtained was incorporated into 1 kg of a high speed silver iodobromide emulsion (containing 3.0 mol% of AgI), followed by addition thereto, as a hardener, of 35 ml of a 3% methanol solution of 1,3,5-triacryloyl-hexahydro-S-triazine. The emulsion thus resulted was coated on a cellulose triacetate base and then dried to obtain a light-sensitive color photographic material having a stable coating thereon.

Each of the light-sensitive color photographic materials obtained in the above manner was wedgewise exposed and then subjected to development treatment according to the following manner.

| Processing step (38° C.) | Processing time |
|---|---|
| Color development | 3 min. 15 sec. |
| Bleaching | 6 min. 30 sec. |
| Water-washing | 3 min. 15 sec. |

| Processing step (38° C.) | Processing time |
|---|---|
| Fixing | 6 min. 30 sec. |
| Water-washing | 3 min. 15 sec. |
| Stabilizing | 1 min. 30 sec. |

The composition of each processer in the above processing steps was as in the following.

Composition of color developer:
| | |
|---|---|
| 4-Amino-3-methyl-N-ethyl-(β-hydroxyethyl)-aniline sulfate | 4.75 g |
| Anhydrous sodium sulfite | 4.25 g |
| Hydroxyamine ½ sulfate | 2.0 g |
| Anhydrous potassium carbonate | 37.5 g |
| Sodium bromide | 1.3 g |
| Nitro-triacetic acid trisodium salt (monohydrate) | 2.5 g |
| Potassium hydroxide | 1.0 g |
| Water is added to make a solution 1 liter and the solution is adjusted to pH 10.0 with potassium hydroxide. | |

Composition of bleach:
| | |
|---|---|
| Ethylenediaminetetraacetic acid iron ammonium salt | 100 g |
| Ethylenediaminetetraacetic acid diammonium salt | 10 g |
| Ammonium bromide | 150 g |
| Glacial acetic acid | 10.0 ml |
| Water is added to make a solution 1 liter and the solution is adjusted to pH 6.0 with ammonia water. | |

Composition of fixer:
| | |
|---|---|
| Ammonium thiosulfate (50% aq. soln.) | 162 ml |
| Anhydrous sodium sulfite | 12.4 g |
| Water is added to make a solution 1 liter and the solution is adjusted to pH 6.5 with acetic acid. | |

Composition of stabilizer:
| | |
|---|---|
| Formalin (37% aq. soln.) | 5.0 ml |
| Konidaks (produced by Konishiroku Photo Industry Co., Ltd.) | 7.5 ml |
| Water is added to make a solution 1 liter. | |

Each of the images thus obtained was measured in density under an interference light having 436 nm, 546 nm and 644 nm, respectively, to obtain the results as shown in Table 1 wherein the densities were represented by relative values as measured under the light having 436 nm and 644 nm, respectively, while assuming as 100 the density of the image as measured under the light having 546 nm at a step where said density was about 1.0.

Comparative compound (1)

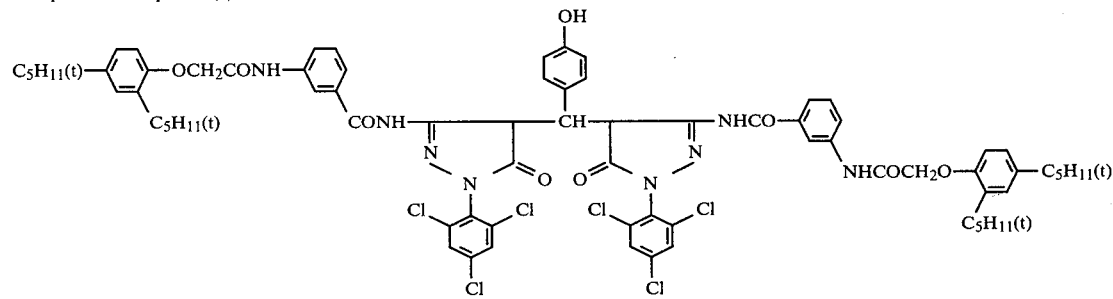

Comparative compound (2)

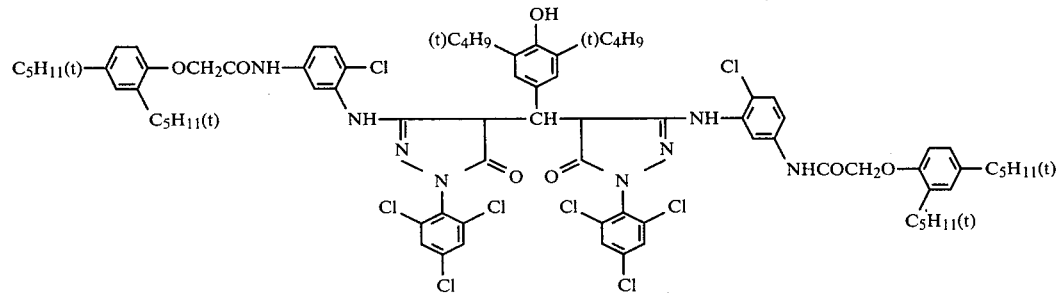

Comparative compound (3)

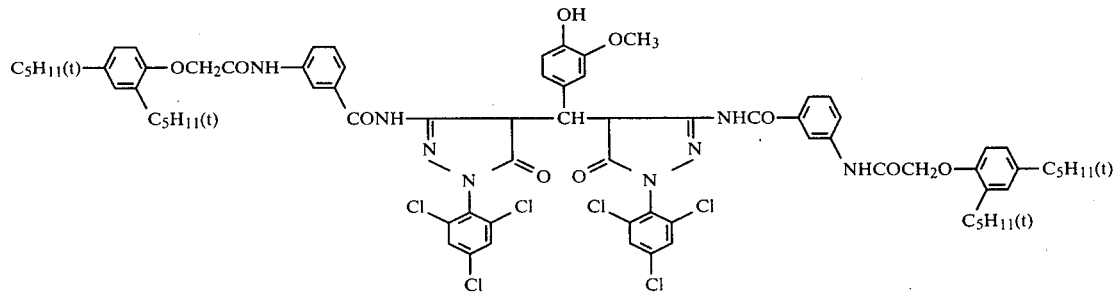

Comparative compound (4)

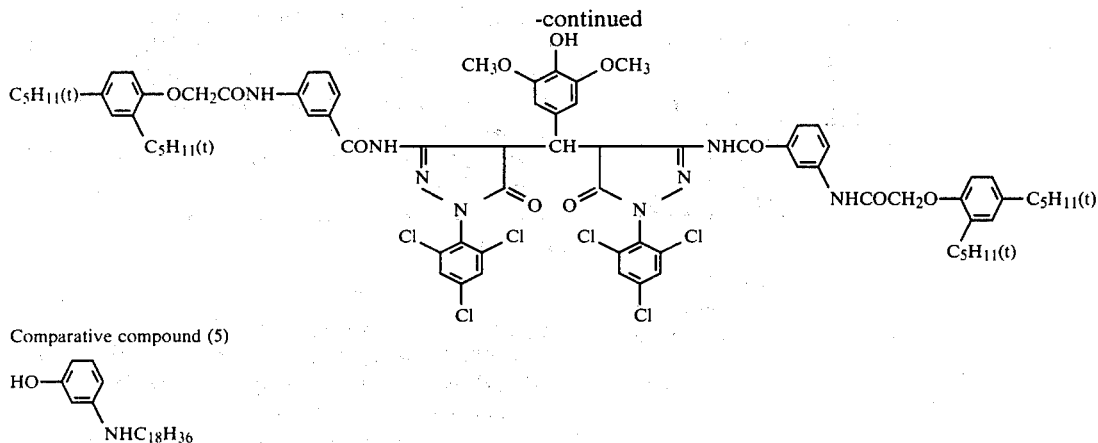

Comparative compound (5)

HO—⟨⟩—NHC₁₈H₃₆

TABLE 1

| | | Density measured under light of 436 nm | Density measured under light of 644 nm |
|---|---|---|---|
| Exemplified compound | (21) | 110 | 65 |
| Exemplified compound | (24) | 108 | 76 |
| Comparative compound | (1) | 22 | 14 |
| Comparative compound | (2) | 20 | 13 |
| Comparative compound | (3) | 305 | 83 |
| Comparative compound | (4) | 279 | 80 |
| Comparative compound | (5) | 62 | 96 |

Images obtained by the use of exemplified compounds (21) and (24), respectively, are both black. Images obtained by the use of comparative compounds (1) and (2), respectively, are both magenta, an image obtained by the use of comparative compound (3) is yellow, an image obtained by the use of comparative compound (4) is yellowish green, and an image obtained by the use of comparative compound (5) is bluish black. This fact shows that no black images can be obtained by the use of known bis-type pyrazolones similar in structure to the compounds of the present invention. Further, comparative compound (5) is a known coupler capable of giving a black image as disclosed in Japanese Laid-Open-to-Public Publication No. 46029/1978. The images obtained by the use of the present compounds, however, assume a more neutral black color than that obtained by the use of the comparative compound (5).

EXAMPLE 2

In a mixture comprising 10 ml of dibutyl phthalate and 30 ml of ethyl acetate was thoroughly dissolved at 40° C. 10 g of exemplified compound (21). The thus prepared solution was mixed with 5 ml of a 10% aqueous solution of Alkanol B (a product of alkyl naphthalene sulfonate produced and sold by Du Pont Co.) and 200 ml of a 5% aqueous gelatin solution, and the resulting mixture was dispersed while emulsifying with a colloid mill to prepare a coupler dispersion. The coupler dispersion thus prepared was incorporated into 500 g of a silver iodobromide emulsion for general black-and-white negative (containing 5 mol% of silver iodide), followed by addition thereto of 20 ml of a solution of a hardener, and the emulsion was then coated on a cellulose triacetate base so that the amount of silver coated became about 20 mg per 100 cm² (sample A). For comparison, on the other hand, the same emulsion as used above but not containing the dispersion of the exemplified compound (21) was coated on a cellulose triacetate base so that the compound of silver coated became about 40 mg/100 cm² (sample B for a comparison).

After having been subjected to wedgewise exposure in the usual way, samples A and B were individually developed at 20° C. for 6 minutes with a developer having the following composition.

| | |
|---|---|
| Methol | 2.5 g |
| Anhydrous sodium sulfite | 30 g |
| Hydroquinone | 2.5 g |
| Sodium carbonate monohydrate | 10 g |
| Potassium bromide | 0.5 g |
| Water to make | 1 liter |

After development, the developed samples were individually subjected, according to the conventional method, to stopping, fixing and water-washing, respectively. The thus obtained samples were designated as A-1 and B-1, respectively. Separately, the aforesaid sample A after exposure was developed at 20° C. for 6 minutes with a developer of the following composition.

| | |
|---|---|
| 4-Amino-3-methyl-N-ethyl-N-methanesulfonamidoethyl aniline 3/2H₂SO₄ | 5 g |
| Anhydrous sodium sulfite | 25 g |
| Sodium carbonate monohydrate | 20 g |
| Potassium bromide | 0.5 g |
| 1-Phenyl-3-pyrazolidone | 0.5 g |
| Water to make | 1 liter |

After development, the developed sample was subjected, according to the conventional method, to stopping, fixing and water-washing, respectively, and the thus obtained sample was designated as A-2.

The sample A-2 was found to give a black image. Sensitometrical results obtained for the samples as prepared above were as shown in Table 2.

TABLE 2

| Sample | Photographic characteristics | | | |
|---|---|---|---|---|
| | *Relative speed | γ | Fog | D max |
| A - 1 (Comparison) | 64 | 0.20 | 0.03 | 1.2 |
| A - 2 (Present invention) | 110 | 0.49 | 0.06 | 2.8 |
| B - 1 (Comparison) | 100 | 0.41 | 0.05 | 2.6 |

*The relative speed was represented by a relative value as measured by assuming as 100 the speed of sample B - 1.

As is clear from Table 2, it was observed that the amount of silver used in sample A-2 according to the present invention was only half that of control sample B-1, nevertheless the maximum density (Dmax) of the sample A-2 as measured was practically on the same level as in the sample B-1.

EXAMPLE 3

The coupler dispersion as prepared in Example 2 was incorporated into 500 g of a low speed silver chlorobromide emulsion for use in puttin-in of photolithographic material, followed by addition thereto of 20 ml of a solution of a hardener, and the emulsion was then coated on a cellulose triacetate base so that the amount of silver coated became about 20 mg/100 cm$^2$ (sample C). Separately, the same emulsion as used above but not containing the coupler dispersion was used for comparison by coating said emulsion on a cellulose triacetate base so that the amount of silver coated became about 50 mg/100 cm$^2$ (sample D). The amount of silver used in sample D is approximately the same as that of photolithographic products currently manufactured, whereas sample C is a low silver content light-sensitive photographic material which contains silver halide only 2/5 that contained in the sample D.

The samples C and D were individually brought into intimate contact with a halftone negative and, after exposure with a printer, developed at 20° C. for 2 minutes 30 seconds with a developer of the following composition.

| | |
|---|---|
| Methol | 1.5 g |
| Anhydrous sodium sulfite | 23 g |
| Hydroquinone | 6 g |
| Sodium carbonate monohydrate | 41 g |
| Potassium bromide | 1.0 g |
| Water to make | 1 liter |

After development, the samples were subjected in the usual way to fixing the water-washing, respectively, and the samples thus obtained were designated as C-1 and D-1, respectively. Separately, sample C which had been exposed in the same manner as above was color developed at 20° C. for 2 minutes 30 seconds with a developer of the following composition.

| | |
|---|---|
| 4-Amino-N,N-diethylaniline ½ H$_2$SO$_4$ | 8 g |
| Sodium carbonate monohydrate | 40 g |
| 1-Phenyl-3-pyrazolidone | 0.3 g |
| Anhydrous sodium sulfite | 20 g |
| Potassium bromide | 1.5 g |
| Water to make | 1 liter |

After development, the sample C was subjected in the usual way to fixing and water-washing, respectively, and the sample thus treated was designated as C-2. From the observational results obtained, it was found that in comparison with the sampel D-1 as a control, the sample C-1 was not only low in density of halftone dot but also poor in quality of the halftone dot, per se. In the case of the sample C-2 which was similarly the sample C but subjected to color development in the manner as mentioned above, however, because the black color formed thereby was heightened due to the color development, the sample C-2 was found to be equal in density as well as quality of the halftone dot to the sample D-1 as a comparison.

EXAMPLE 4

In a mixture comprising 10 ml of tricresyl phosphate and 30 ml of ethyl acetate was thoroughly dissolved at 50° C. 10 g of exemplified compound (21). The solution thus obtained was mixed with 5 ml of a 10% aqueous solution of Alkanol B and 200 ml of a 5% aqueous gelatin solution and emulsified with a colloid mill to prepare a coupler dispersion. This coupler dispersion was incorporated into 500 g of a silver iodobromide (containing 5 mol% of silver iodide) emulsion for X-ray photography, followed by addition thereto of 20 ml of a solution of a hardener. The emulsion was then coated on one side of a polyester base so that the amount of silver coated bacame 40 mg/100 cm$^2$ (sample E). Separately, the same emulsion as prepared above but not containing the exemplified compound (21) was coated on one side of a polyester base so that the amount of silver became 40 mg/100 cm$^2$, and the sample thus prepared was designated as a control sample F.

After having been wedgewise exposed, the sampel F was developed at 20° C. for 5 minutes with a developer of the following composition, followed by fixing and water-washing in the usual way.

| | |
|---|---|
| Anhydrous sodium sulfite | 60 g |
| 1-Phenyl-3-pyrazolidone | 0.3 g |
| Hydroquinone | 15 g |
| Anhydrous sodium carbonate | 25 g |
| Potassium bromide | 4 g |
| Benztriazole | 0.3 g |
| Sodium hydroxide | 25 g |
| Water to make | 1 liter |

On the other hand, the sample E which had been similarly exposed was subjected at 20° C. for 5 minutes to color development with a developer of the composition mentioned below, followed by fixing and water-washing in the usual way.

| | |
|---|---|
| 4-Amino-N,N-diethylaniline ½ H$_2$SO$_4$ | 8 g |
| Anhydrous sodium sulfite | 25 g |
| Potassium bromide | 3 g |
| 1-Phenyl-3-pyrazolidone | 0.3 g |
| Hydroquinone | 3 g |
| Anhydrous sodium carbonate | 5.0 g |
| Water to make | 1 liter |

As a result of the processing, the sample E was found to comprise a black dye image and a silver image, and the results of a comparison between the present sample E and control sample F were as shown in Table 3 wherein the relative speed was represented by a relative value as measured by assuming as 100 the speed of the sample F.

TABLE 3

| Sample | Photographic characteristics | | | |
|---|---|---|---|---|
| | Relative speed | γ | Fog | Dmax |
| E (Present invention) | 120 | 2.8 | 0.05 | 2.4 |
| F (Control) | 100 | 1.2 | 0.03 | 1.2 |

As is clear from Table 3, it is understood that a light-sensitive silver halide photographic material has, as a light-sensitive material for X-ray photography, excellent properties.

EXAMPLE 5

The same samples as used in Example 4 were individually subjected to the same treatment as in Example 4 except that 4-amino-N,N-diethylaniline was changed by p-aminophenol.

As a result of the treatment, the sample E was found to comprise a black dye image with a brownish tone and a developed silver image, and a comparison in maximum density (Dmax) between the samples E and F was made to give the results as shown in Table 4.

TABLE 4

| Sample | Dmax |
|---|---|
| E | 2.3 |
| F | 1.2 |

EXAMPLE 6

Into a silver chlorobromide emulsion for general black-and-white printing paper was incorporated a dispersion of exemplified compound (21), followed by addition thereto of a solution of a hardener, and the emulsion was coated in the manner as shown in Table 5 on a cellulose triacetate base. On the emulsion layer thus formed was formed a protective layer comprising gelatin, a hardener and an extender (samples G, H and I).

TABLE 5

| Sample | Amount of silver added mg/100 cm² | Amount of the present compound added mg/100 cm² |
|---|---|---|
| G (Control) | 13 | 0 |
| H | 6 | 10 |
| I | 1.5 | 10 |

The samples G, H and I were individually subjected to wedgewise exposure, followed by developing at 20° C. for 1 minute with a developer of the following composition.

| Methol | 1 g |
|---|---|
| Anhydrous sodium sulfite | 7.5 g |
| Hydroquinone | 4 g |
| Sodium carbonate monohydrate | 26.7 g |
| Potassium bromide | 0.7 g |
| Water to make | 1 liter |

After development, the samples G, H and I were individually subjected to stopping, fixing and water-washing, respectively, in the usual way, and the samples thus processed were designated as samples Nos. 1, 2 and 3 respectively. Separately, the samples H and I as prepared above were individually subjected to wedgewise exposure, followed by developing at 20° C. for 1 minute with a developer of the following composition.

| 4-Amino-N,N-diethylaniline ½ H₂SO₄ | 4 g |
|---|---|
| Anhydrous sodium sulfite | 4 g |
| Sodium carbonate monohydrate | 25 g |
| Potassium bromide | 1.0 g |
| 1-Phenyl-3-pyrazolidone | 0.3 g |
| Water to make | 1 liter |

The samples H and I were individually subjected to stopping, fixing and water-washing, respectively, in the usual way, and the samples thus processed were designated as samples Nos. 4 and 5 respectively.

Furthermore, the sample I as prepared previously was wedgewise exposed and developed at 20° C. for 1 minute with the above-mentioned color developer to which had been added 2.0 g/liter of hexaamino-cobalt chloride, followed by stopping, fixing and water-washing, respectively, in the usual way, and the sample I thus treated was designated as sample No. 6.

The samples thus prepared were individually measured in maximum density to obtain the results as shown in Table 6.

TABLE 6

| Sample No. | Relative speed | Dmax |
|---|---|---|
| 1 (Control) | 100 | 1.4 |
| 2 | 62 | 0.6 |
| 3 | — | — |
| 4 | 175 | 1.5 |
| 5 | — | — |
| 6 | 113 | 1.6 |

In the above Table, — means that they are too low to measure.

As can be seen from the foregoing, it is understood that in case of using the present compound (sample No. 4), the amount of silver used may be reduced to by about one half even when the sample is subjected to an ordinary color development and, moreover, the amount of silver used can be reduced more sharply when the sample (No. 6) is developed with the color developer using hexaamino-cobalt chloride in combination therewith.

EXAMPLE 7

Silver halide emulsions were individually coated on a polyester base in the proportions as shown in the following Table 7 to prepare samples J, K, L and M, respectively.

TABLE 7

| Sample | Amount of silver used mg/100 cm² | Amount of the present Compound added mg/100 cm² |
|---|---|---|
| J | 40 | — |
| K | 5 | — |
| L | 40 | 10 |
| M | 5 | 10 |

Each of the samples as prepared above was further coated on the emulsion layer with a gelatin protective layer containing a hardener, an extender, etc., and the silver halide emulsion used in forming the emulsion layer was a silver iodobromide emulsion for use in X-ray photography. In the case of the sample L as well as of M, the exemplified compound (21) was used by protect dispersing it by the use of tricresyl phosphate in the emulsion according to the manner similar to that of Example 1.

After having been wedgewise exposed, the sample J was developed at 20° C. for 5 minutes with the same monochromatic developer as used in Example 4, followed by fixing and water-washing, respectively, in the usual way, and the sample thus prepared was designated as sample No. 7 (control). After having been processed in the same manner as in the case of the sample No. 7, the sample K as prepared was designated as sample No. 8. The samples L and M were individually developed at 20° C. for 5 minutes with the same color developer as used in Example 6, followed by fixing and water-washing, respectively, in the similar manner, and the thus processed samples were designated as samples Nos. 9 and 10 respectively. Separately, the samples L and M as prepared were individually developed at 20° C. for 5 minutes with a developer of the following composition.

| | |
|---|---|
| 4-Amino-N,N-diethylaniline ½ $H_2SO_4$ | 7 g |
| Anhydrous sodium sulfite | 20 g |
| Anhydrous sodium carbonate | 50 g |
| Hydroquinone | 5 g |
| 1-Phenyl-3-pyrazolidone | 0.5 g |
| N-Methylbenzthiazolium-p-toluenesulfonate | 1.0 g |
| 1-Phenyl-5-mercaptotetrazole | 20 mg |
| Water to make | 1 liter |

The samples L and M thus developed were individually subjected to fixing and water-washing, respectively, in the usual way, and the samples thus prepared were designated as samples Nos. 11 and 12 respectively. Of the samples L and M as developed, the sample L was further processed at 20° C. for 6 minutes with a hydrogen peroxide bath of the following composition, followed by fixing and water-washing, respectively, in the similar manner, and the sample thus prepared was designated as sample No. 13.

35% $H_2O_2$—25 ml

Water to make the resulting solution 1 liter and the solution is adjusted to pH 8 with 1N-NaOH.

The samples as prepared above were individually measured in fog as well as im maximum density to obtain the results as assembled in Table 8.

TABLE 8

| Sample No. | Coating conditions A-mount of silver | Present compound | Monochromatic development | Color development | $H_2O_2$ treatment | Result Fog | Dmax |
|---|---|---|---|---|---|---|---|
| 7 (Control) | 40 mg | — | Employed | Unemployed | Unemployed | 0.04 | 1.1 |
| 8 | 5 mg | — | Employed | Unemployed | Unemployed | — | — |
| 9 | 40 mg | 10 mg | Unemployed | Employed | Unemployed | 0.05 | 2.4 |
| 10 | 5 mg | " | Unemployed | Employed | Unemployed | — | — |
| 11 | 40 mg | " | Unemployed | Employed | Unemployed | 0.05 | 2.7 |
| 12 | 5 mg | " | Unemployed | Employed | Unemployed | — | — |
| 13 | 5 mg | " | Unemployed | Employed | Employed | 0.07 | 3.0 |

Reviewing the results from Table 8, it is understood that a drastic cut in amount of silver of the light-sensitive silver halide monochromatic photographic material becomes possible by the combinational use of the present compound and the hydrogen peroxide amplifying bath.

EXAMPLE 8

Samples O, P and Q were individually prepared by applying to a support a low speed silver chlorobromide emulsion for printing paper and a dispersion of exemplified compound (21) in an alkali solution in the proportions as indicated in Table 9.

TABLE 9

| | Coating proportion | |
|---|---|---|
| Sample | Silver mg/100 $cm^2$ | Present compound mg/100 $cm^2$ |
| O (Control) | 40 | — |
| P | 20 | 8 |
| Q | 4 | 8 |

Separately, 15 ml of a 5% aqueous solution of DES [sodium di-(ethylhexyl succinate)-sulfonate], 60 ml of a 10% aqueous gelatin solution, 200 mg of chloro-1,3,5-triphenyltetrazolium (hereinafter called "T-salt" for short) and 35 ml of water were subjected to ultrasonic wave dispersion to prepare a dispersion. The dispersion thus prepared was incorporated into a mixture of the aforesaid emulsion and coupler dispersion, and the resulting mixture was coated on a cellulose triacetate base in the proportions as indicated in Table 10 to prepare samples R, S and T respectively.

TABLE 10

| | Coating proportion | | |
|---|---|---|---|
| Sample | Silver mg/100 $cm^2$ | Present compound mg/100 $cm^2$ | Cloro-1,3,5-triphenyltetrazolium mg/100 $cm^2$ |
| R | 40 | — | 2 |
| S | 20 | 8 | 2 |
| T | 4 | 8 | 2 |

Samples O, P, Q, R, S and T as prepared above were individually subjected to ordinary halftone dot exposure and then processed in the following manner. The samples O and P were individually developed at 20° C. for 2 minutes and 30 seconds with a developer of the following composition, followed by fixing and water-washing, respectively, in the usual way, and the thus obtained samples were designated as samples Nos. 14 and 17 respectively.

| | |
|---|---|
| Methol | 1.5 g |
| Anhydrous sodium sulfite | 20 g |
| Hydroquinone | 6 g |
| Sodium carbonate monohydrate | 40 g |
| Potassium bromide | 1.0 g |
| Water to make | 1 liter |

The samples P and S were individually developed at 20° C. for 2 minutes 30 seconds with a developer of the following composition, followed by fixing and then water-washing in the usual way, and the samples thus obtained were designated as samples Nos. 15 and 18 respectively.

| | |
|---|---|
| 4-Amino-N,N-diethylaniline ½ $H_2SO_4$ | 7 g |

-continued

| | |
|---|---|
| 1-Phenyl-3-pyrazolidone | 0.5 g |
| Anhydrous sodium sulfite | 20 g |
| Sodium carbonate monohydrate | 40 g |
| Potassium bromide | 1.0 g |
| Water to make | 1 liter |

The samples Q and P, after having been developed in the same manner as in the case of the samples Nos. 15 and 18 with the developer mentioned above, were individually processed at 20° C. for 5 minutes with a hydrogen peroxide amplifying bath of the following composition, followed by fixing and then water-washing, and the samples as obtained were designated as samples Nos. 16 and 19 respectively.

35% $H_2O_2$—25 ml

Water is added to make a solution 1 liter and the solution is adjusted to pH 8 with 1 N-NaOH.

The results of measurements obtained were as assembled in Table 11.

TABLE 11

| | Coating conditions | | | Treatment conditions | | | Result | |
|---|---|---|---|---|---|---|---|---|
| Sample No. | Silver | Present compound | T-salt | Monochromatic development | Color development | $H_2O_2$ treatment | Dmax | Halftone |
| 14 | 40 mg | — | — | Employed | Unemployed | Unemployed | 1.9 | Bad |
| 15 | 20 mg | 8 mg | — | Unemployed | Employed | Unemployed | 2.1 | Bad |
| 16 | 4 mg | 8 mg | — | Unemployed | Employed | Employed | 2.7 | Bad |
| 17 | 40 mg | — | 2 mg | Employed | Unemployed | Unemployed | 1.9 | Good |
| 18 | 20 mg | 8 mg | 2 mg | Unemployed | Employed | Unemployed | 2.0 | Good |
| 19 | 4 mg | 8 mg | 2 mg | Unemployed | Employed | Employed | 2.6 | Good |

From the results as obtained above, it is understood that the samples containing T-salt all give halftone dots favorable in image quality even when processed with a general developer which is not a special developer for use in developing lightsensitive photographic printing material, and that the sample containing T-salt in combination with the present coupler gives a sufficient density as well as a halftone dot favorable in image quality even when the amount of silver in said sample is reduced to half and, moreover, said amount of silver can be more sharply reduced when said sample is processed with the hydrogen peroxide amplifying bath.

EXAMPLE 9

Exemplified compound (25) was alkali-dispersed in the usual way, and the dispersion thus obtained was incorporated into a silver iodobromide (containing 5 mol% of silver iodide) emulsion for X-ray photography and the emulsion was coated on one side of a polyester base in the proportion as indicated in Table 12 to prepare samples V and W respectively.

Separately, a sample was prepared in the same manner as above using the same emulsion but without incorporating thereinto the present compound, and the sample was designated as sample U as a control.

TABLE 12

| | Coating proportion | |
|---|---|---|
| Sample | Silver mg/100 cm$^2$ | Present compound mg/100 cm$^2$ |
| U (Control) | 40 | — |
| V | 40 | 13 |
| W | 7 | 13 |

The sample U was developed at 20° C. for 5 minutes with a monochromatic developer of the same composition as in the developer used in Example 4, followed by fixing and water-washing, respectively, and the sample thus processed was designated as sample No. 20 (control).

The sample V was developed at 20° C. for 5 minutes with a color developer of Example 4 containing 4-amino-N,N-diethylaniline, followed by fixing and water-washing, respectively, and the sample this processed was designated as sample No. 21.

After having been color developed in the same manner as in the case of the sample V, the sample W was processed at 20° C. for 5 minutes with a hydrogen peroxide amplifying bath of the same composition as used in Example 8, and the thus processed sample was designated as sample 22.

The results of measurements in photographic properties of these samples were as shown in Table 13.

TABLE 13

| | Photographic properties | |
|---|---|---|
| Sample No. | Fog | Dmax |
| 20 | 0.03 | 1.3 |
| 21 | 0.04 | 2.5 |
| 22 | 0.05 | 2.5 |

As is clear from Table 13, the object of the present invention can be accomplished as well by the use of the alkali dispersion type coupler according to the present invention, and the amount of silver in the light-sensitive silver halide photographic materials of the present invention can be cut to about half when the materials are intended to be subjected to ordinary color development and, moreover, sharp curtailment of the silver amount is possible when intended to be color developed, followed by processing with a hydrogen peroxide amplifying bath.

EXAMPLE 10

Following the procedure as employed in Example 4, a sample was prepared by forming on a polyethylene terephthalate base a silver halide emulsion layer and a protective layer in the following coating proportions.

| (1) | High speed silver iodobromide emulsion for X-ray photography | |
|---|---|---|
| | Gelatin | 19 mg/dm² |
| | Silver | 25 mg/dm² |
| | Exemplified compound (21) | 16 mg/dm² |
| (2) | Gelatin protective layer | 11 mg/dm² |

Subsequently, the sample thus prepared was wedge-wise exposed, followed by development at 20° C. for 3 minutes with a developer of the following composition.

| 4-Amino-N,N-diethylaniline sulfate | 6 g |
|---|---|
| Sodium carbonate monohydrate | 10 g |
| Potassium bromide | 1.0 g |
| Sodium sulfite | 10 g |
| 5-Nitrobenzimidazole | 150 mg |
| Distilled water to make a solution 1 liter and the solution is adjusted to pH 11.0 with sodium hydroxide. | |

The sample thus developed was subjected to stopping, fixing, water-washing and drying in the usual way to obtain a negative bearing thereon a black dye image. The negative thus obtained was measured in fog and maximum density (Dmax) to obtain the results as shown below.

| Fog | 0.07 |
|---|---|
| Dmax | 2.3 |

From the above results, it is understood that as compared with conventional X-ray films, the present photographic material can make it possible to drastically curtail the amount of silver to be used (to about 1/66).

EXAMPLE 11

A green-sensitive silver iodobromide emulsion for X-ray photography and exemplified compound (21) having been incorporated thereinto were coated on a polyethyleneterephthalate base and thereon was coated a protective layer in the following coating proportions, to obtain a sample having the support and the silver halide and protective layers in that order.

| (1) | Gelatin | 23 mg/dm² |
|---|---|---|
| | Silver | 21 mg/dm² |
| | Exemplified compound (21) | 15 mg/dm² |
| (2) | Gelatin protective layer | 10 mg/dm² |

The sample thus prepared was exposed using a GTH ortho type sensitizing paper (manufactured and sold by Tokyo Shibaura Elect. Co.) through an aluminum wedge to X-ray of 70 KUP and 100 MA at a distance of 1 meter from the ray source.

The sample thus exposed was color developed at 20° C. for 3 minutes with the same developer as used in Example 10, followed by fixing, water-washing and drying, respectively, in the usual way. Subsequently, the image formed on the thus processed sample was measured in fog, maximum density (Dmax) and γ to obtain the results as shown below.

| Fog | 0.05 |
|---|---|
| Dmax | 2.6 |
| γ | 2.7 |

From the results mentioned above, it was understood that the image is an image of a black dye color and a curtailment of the photographic material of the present invention, even when it is used as an ortho type X-ray film, in its silver conten to ¼ of that used in currently available X-ray films becomes possible as well without causing any deterioration in image quality of the resulting image.

What we claim is:

1. A process for forming a due image comprising processing an image-wise exposed silver halide photographic emulsion with an aromatic primary amine color developing agent in the presence of bis-type pyrazolones obtained by reacting 3-acylamino-5-pyrazolones with para-hydroxybenzaldehydes, at least one of the ortho-positions of the hydroxy group of which has been substituted with a halogen atom, an alkyl, aryl, amino or amido group.

2. A process for forming a dye image according to claim 1 wherein the bis-type pyrazolones are represented by the following general formula[I]:

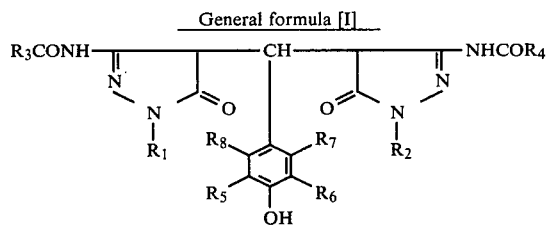

General formula [I]

wherein $R_1$ and $R_2$, which may be the same or different, individually represent a hydrogen atom, an alkyl, aryl or heterocyclic group, $R_3$ and $R_4$, which may be the same or different, individually represent an alkyl, aryl, heterocyclic, substituted oxy or amino group, $R_5$ represents a halogen atom, an alkyl, aryl, amino or amido group, and $R_6$, $R_7$ and $R_8$ individually represent a hydrogen or halogen atom, an alkyl, aryl, substituted oxy, alkyl or amino group.

3. A process for forming a dye image according to claim 2 wherein $R_1$ and $R_2$ are the same and $R_3$ and $R_4$ are the same in the general formula [I].

4. A process for forming a dye image according to claim 2 or 3 wherein $R_7$ and $R_8$ are simultaneously hydrogen atoms in the general formula [I].

5. A process for forming a dye image according to claim 4 wherein $R_6$ is a halogen atom, an alkyl, aryl, substituted oxy, amino or amido group in the general formula [I].

6. A process for forming a dye image according to claim 2 wherein $R_1$ and $R_2$ individually represent an unsubstituted or substituted aryl group.

7. A process for forming a dye image according to claim 1 wherein $R_3$ and $R_4$ individually represent an unsubstituted or substituted aryl group.

8. A process for forming a dye image according to claim 2 wherein $R_5$ and $R_6$ individually represent a branched alkyl group.

9. A process for forming a dye image according to claim 8 wherein $R_5$ and $R_6$ individually represent a t-butyl or t-pentyl group.

10. A photographic material having a silver halide emulsion layer coated on a support which material comprises a dye forming coupler represented by the following general formula [I]:

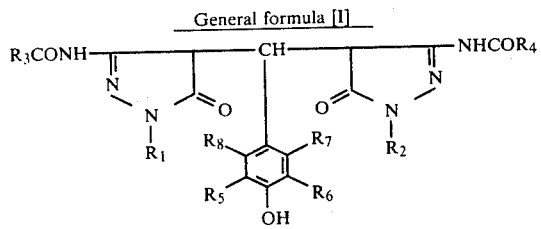

General formula [I]

wherein $R_1$ and $R_2$, which may be the same or different, individually represent a hydrogen atom, an alkyl, aryl or heterocyclic group, $R_3$ and $R_4$, which may be the same or different, individually represent an alkyl, aryl, heterocyclic, substituted oxy or amino group, $R_5$ represents a halogen atom, an alkyl, aryl, amino or amido group, and $R_6$, $R_7$ and $R_8$ individually represent a hydrogen or halogen atom, an alkyl, aryl, substituted oxy, alkyl or amino group.

11. A photographic material according to claim 10 wherein $R_1$ and $R_2$ are the same and $R_3$ and $R_4$ are the same in the general formula [I].

12. A photographic material according to claim 10 or 11 wherein $R_7$ and $R_8$ are simultaneously hydrogen atoms in the general formula [I].

13. A photographic material according to claim 10 wherein $R_6$ is a halogen atom, an alkyl, aryl, substituted oxy, amino or amido group in the general formula [I].

14. A photographic material according to claim 10 wherein $R_1$ and $R_2$ individually represent an unsubstituted or substituted aryl group.

15. A photographic material according to claim 10 wherein $R_3$ and $R_4$ individually represent an unsubstituted or substituted aryl group.

16. A photographic material according to claim 10 wherein $R_5$ and $R_6$ individually represent a branched alkyl group.

17. A photographic material according to claim 16 wherein $R_5$ and $R_6$ individually represent a t-butyl or t-pentyl group.

18. A photographic material according to claim 10 wherein the dye forming coupler is represented by the following formula:

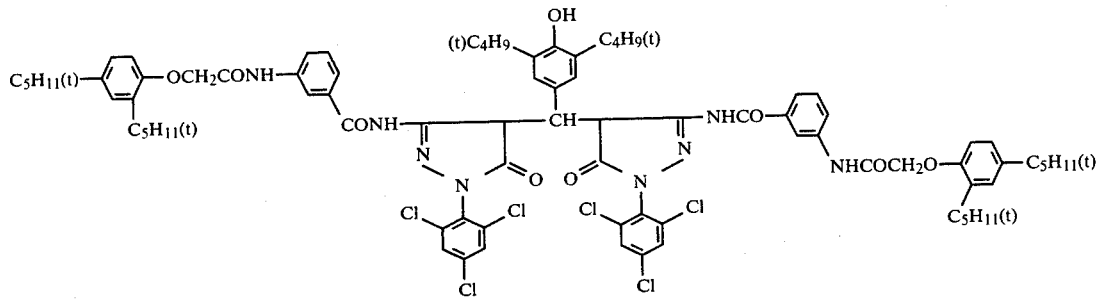

* * * * *